(12) United States Patent
Beaudouin (10) Patent No.: US 9,655,986 B2
(45) Date of Patent: May 23, 2017

(54) DEVICE AND METHOD FOR THE TREATMENT OF A GASEOUS MEDIUM AND USE OF THE DEVICE FOR THE TREATMENT OF A GASEOUS MEDIUM, LIQUID, SOLID, SURFACE OR ANY COMBINATION THEREOF

(76) Inventor: Jean-Michel Beaudouin, Zürich (CH)

( * ) Notice: Subject to any disclaimer, the term of this patent is extended or adjusted under 35 U.S.C. 154(b) by 1001 days.

(21) Appl. No.: 13/820,011

(22) PCT Filed: Sep. 1, 2011

(86) PCT No.: PCT/EP2011/065120
§ 371 (c)(1),
(2), (4) Date: Sep. 24, 2013

(87) PCT Pub. No.: WO2012/028687
PCT Pub. Date: Mar. 8, 2012

(65) Prior Publication Data
US 2014/0010707 A1    Jan. 9, 2014

(30) Foreign Application Priority Data
Sep. 2, 2010  (WO) .................. PCT/EP2010/062870

(51) Int. Cl.
*A61L 9/22*      (2006.01)
*A61L 2/14*      (2006.01)
(Continued)

(52) U.S. Cl.
CPC ...... *A61L 2/14* (2013.01); *A61L 9/22* (2013.01); *B01D 53/007* (2013.01); *B01D 53/32* (2013.01);
(Continued)

(58) Field of Classification Search
CPC ... A61L 2/14; A61L 9/22; H01J 25/50; B01D 53/007; B01D 53/32; B01D 53/44; B01D 2259/818; H01H 1/46; H05H 2245/121
See application file for complete search history.

(56) References Cited

U.S. PATENT DOCUMENTS 4,822,450 A     4/1989  Davis et al.
5,763,763 A *   6/1998  Kato .................. G01N 27/4074
                                                    204/412

(Continued)

FOREIGN PATENT DOCUMENTS

EP       1565044       8/2005
EP       1813351       8/2007
(Continued)

OTHER PUBLICATIONS

Akimov, "Effect of Secondary Electron Emission on Surface Wave Propagation", IEEE Transactions on Plasma Science, vol. 33, No. 1, Feb. 2005, XP007918692.
(Continued)

*Primary Examiner* — Timothy Cleveland
(74) *Attorney, Agent, or Firm* — Davis & Bujold PLLC; Michael Bujold (57) ABSTRACT

The device for the treatment of a gaseous medium according to the invention comprises in flow direction of the gaseous medium a plasma-generating device for the generation of a plasma in the gaseous medium. The plasma comprises in particular excited molecules, radicals, ions, free electrons, photons and any combination thereof. Furthermore, the device according to the invention comprises at least one dielectric structure, in particular at least one fused silica tube. The plasma is conveyable into the at least one dielectric structure, in particular after generation in the plasma-generating device.

20 Claims, 5 Drawing Sheets

(51) Int. Cl.
    *B01D 53/00*     (2006.01)
    *B01D 53/32*     (2006.01)
    *B01D 53/44*     (2006.01)
    *H05H 1/46*     (2006.01)
    *H01J 25/50*     (2006.01)

(52) U.S. Cl.
    CPC .............. *B01D 53/44* (2013.01); *H01J 25/50* (2013.01); *H05H 1/46* (2013.01); *B01D 2257/91* (2013.01); *B01D 2259/804* (2013.01); *B01D 2259/806* (2013.01); *B01D 2259/818* (2013.01); *H05H 2245/121* (2013.01)

(56) References Cited

U.S. PATENT DOCUMENTS

| | | | |
|---|---|---|---|
| 2003/0141182 A1 | 7/2003 | Kong et al. | |
| 2003/0157000 A1 | 8/2003 | Janssen et al. | |
| 2005/0133927 A1 | 6/2005 | Rosocha et al. | |
| 2005/0274599 A1 | 12/2005 | Tamura et al. | |
| 2007/0284242 A1* | 12/2007 | Moisan | B01D 53/32 204/165 |
| 2008/0169183 A1 | 7/2008 | Hertel et al. | |
| 2009/0223806 A1 | 9/2009 | Thevenet et al. | |
| 2010/0254853 A1* | 10/2010 | Lee | A61L 2/14 422/29 |

FOREIGN PATENT DOCUMENTS

| | | |
|---|---|---|
| EP | 2023696 | 2/2009 |
| JP | H01152629 A | 6/1989 |
| JP | 2000228154 A | 8/2000 |
| JP | 2007517650 A | 7/2007 |
| JP | 2009514663 A | 4/2009 |
| JP | 2010009890 A | 1/2010 |
| JP | 2010516062 A | 5/2010 |
| WO | 02/00330 | 1/2002 |
| WO | 2005/079123 A2 | 8/2005 |
| WO | 2007/051912 | 5/2007 |
| WO | 2008089178 A2 | 7/2008 |

OTHER PUBLICATIONS

Bogaerts, "Gas Discharge Plasmas and Their Applications", Spectrochimica Acta Part B 57 (2002), pp. 609-658, Elsevier Science B.V.

Japanese Office Action issued in corresponding Japanese Patent Application No. 2013-526474 mailed Jul. 7, 2015.

Gaudin et al.,"Photoconductivity and Photoemission of Diamond Under Femtosecond VUV Irradiation", (2005), Scientific Commons.

Han et al., "Three-Dimensional Stimulated Emission Depletion Microscopy of Nitrogen-Vacancy Centers in Diamond Using Continuous-Wave Light", Nano Letters, 2009, vol. 9, No. 9, pp. 3323-3329.

Morvova et al., "Plasma Technologies for Reducing CO2 Emissions from Combustion Exhaust with Toxic Admixtures to Utilisable Products", Journal of Thermal Analysis and Calorimetry, vol. 61, (2000), pp. 273-287.

Morvova et al., "Utilisation of CO2, Fixation of Nitrogen and Exhaust Gas Cleaning in Electric Discharge with Electrode Catalysis", Institute of Physics.

Takahashi et al., "Photochemical Abiotic Synthesis of Amino-Acid Precursors from Simulated Planetary Atmospheres by Vacuum Ultraviolet Light", Journal of Applied Physics, Jul. 2005, vol. 98, issue 2.

Civiš et al., "Amino Acid Formation Induced by High-Power Laser in CO2/CO—N2—H2O Gas Mixtures", Chemical Physics Letters 386, (2004), pp. 169-173.

Yanguas-Gil et al., "Reforming of Ethanol in a Microwave Surface-Wave Plasma Discharge", Applied Physics Letters, vol. 85, No. 18, Nov. 1, 2004.

Jasinski et al., "Hydrogen Production Via Methane Reforming Using Various Microwave Plasma Sources", Chem. Listy 102, S. 1332-S. 1337, 2008, II Central European Symposium on Plasma Chemistry 2008.

Gaudin et al.,"Photoconductivity and Photoemission of Diamond Under Femtosecond VUV radiation", (2005), Scientific Commons.

Han et al., "Three-Dimensional Stimulated Emission Depletion microscopy of Nitrogen-Vacancy Centres in Diamond Using Continuous-Wave Light", Nano Letters, 2009, vol. 9, No. 9, pp. 3323-3329.

Morvova et al., Journal of Thermal Analysis and Caloemintry, vol. 61, 2000, pp. 273-287.

Morvova et al., "Utilisation of CO2, Fixation of Nitrogen and Exhaust Gas Cleaning in Electric Discharge with Electrode Catalysers".

Takahachi et al., Journal of Applied Physics, Jul. 2005, vol. 98, issue 2.

Civies et al., Chemical Physics Letters 389, 2004, pp. 169-173.

Yanguas-Gil et al., Applied Physics Letters, vol. 85, No. 18, Nov. 1, 2004.

Jasinski et al., Chiem. Listi 102, S. 1332-S. 1337, 2008.

II Central European Symposium on Plasma Chemistry 2008.

* cited by examiner

DEVICE AND METHOD FOR THE TREATMENT OF A GASEOUS MEDIUM AND USE OF THE DEVICE FOR THE TREATMENT OF A GASEOUS MEDIUM, LIQUID, SOLID, SURFACE OR ANY COMBINATION THEREOF

The present invention is related to a device for the treatment of a gaseous medium with plasma, a method for treatment of said gaseous medium with plasma and the use of both the device and method for treatment of a gaseous medium, liquid, solid, surface or any combination thereof.

Various methods of plasma generation and a vast variety of applications of such plasmas are known in the art, e. g. reviewed by Bogaerts et al., Spectrochimica Acta Part B 57 (2002) 609-658.

It is known in the art to sterilize a gaseous medium by plasma treatment of said gaseous medium, wherein airborne microbes and chemical toxins are destroyed with said plasma as e. g. suggested by WO 2005/079123 A2. With these methods it is for example possible to destroy certain volatile organic compounds (VOC), in particular long-chained VOC.

It is further known in the art to use corona discharge plasmas to sterilize a gaseous medium as suggested by U.S. Pat. No. 5,814,135.

These known devices have the drawback that the achieved sterilizing effect is not sufficient, especially with certain microbes and toxins like e.g. short-chained VOC, which are not normally destructible by the above mentioned devices.

It is thus an object of the present invention to overcome the above-mentioned drawbacks, i.e. to provide a device and a method for treating a gaseous medium that allows for an improved, i.e. enhanced, treatment effect while being energy efficient, i.e. consuming little energy. In particular, this object includes the synthesis and decomposition of molecules, the inactivation or fragmentation of biological structures like proteins, pollen, spores, bacteria or viruses.

These objects are met by a device for the treatment of a gaseous medium with plasma, a method for treatment of a gaseous medium with plasma and the use of both the device and the method for the treatment of the gaseous medium, a liquid, a solid, a surface or any combination thereof according to the independent claims.

Although the invention is not limited thereby, the treatment of a gaseous medium, liquid, solid or a surface thereof with plasma is presently understood as photolysis, i.e. a photolytic reaction; the treatment with plasma is in particular a means for inducing or supporting photolysis by the photons and/or electric forces comprised in the plasma; it is furthermore understood that the efficiency of molecular interactions in or with the plasma for decomposition and/or synthesis of molecules is enhanced by initial destabilization of the molecules and their interaction with one or multiple photons.

Photolysis comprises in particular decomposition and/or synthesis of molecules, in particular bio molecules, and/or inactivation by fragmentation of biomass like micro organisms. As understood here and henceforth, a bio molecule is any organic molecule that is produced by a living organism.

Photolysis means breaking up of molecular bonds with photons, i.e. electromagnetic waves. Commercial applications of photolysis for instance are curing of polymers, destruction of pathogens or gaseous pollutants in liquid or gases or on solid surfaces with photons.

In the context of the present invention, treatment of a gaseous medium, liquid, solid, surface or any combination thereof comprises synthesis of molecules in the gaseous medium, liquid, solid, surface or any combination thereof and/or decontamination of the gaseous medium, liquid, solid, surface or any combination thereof. Decontamination includes for example the reduction of the amount of molecules and/or of biomass like micro organisms in the gaseous medium, liquid, solid, surface or any combination thereof. In particular, treatment comprises the fragmentation of biological structures.

The term synthesis and/or decontamination have in the context of the present invention any of the following meanings: synthesis; decontamination; synthesis and decontamination.

Synthesis comprises inter alia the synthesis of hydrogen ($H_2$) by reforming ethanol and/or methanol.

The device for the treatment of a gaseous medium according to the invention comprises in flow direction of the gaseous medium a plasma-generating device for the generation of a plasma in the gaseous medium. The plasma comprises in particular excited molecules, radicals, ions, free electrons, photons and any combination thereof. Furthermore, the device according to the invention comprises at least one dielectric structure, in particular at least one fused silica tube. The plasma is conveyable into the at least one dielectric structure, in particular after generation in the plasma-generating device.

In particular, the plasma-generating device may be a plasma chamber into which the flow of gaseous medium enters the device according to the invention. The gaseous medium may be the gaseous medium to be treated or a gaseous medium to be used to treat a further gaseous medium, liquid, solid, surface or any combination thereof.

Furthermore, the plasma-generating device comprises in particular a generator for the generation of electromagnetic radiation having a frequency in the radiofrequency range to the microwave range.

The dielectric structure according to the invention is formed such that it is possible to convey a plasma inside the structure and along said structure. In particular, such a structure can be formed as a tube of circular, rectangular or elliptic cross-section. In particular, such a structure can be formed with any cross-section.

In the context of the present application it is to be understood that plasma is a gas and/or vapour that is dissociated into its components under the influence of an electrical field. The plasma thus comprises photons, free electrons, ions, free radicals and neutral particles, in particular excited neutral particles, as well as other constituents. Such a plasma is preferably a non-thermal plasma. In particular, such a plasma has a degree of ionisation of less than 10%, preferably of less than 5%, more preferably of less than 3% and most preferably of less than 1.5%.

Such plasmas may be generated by the device as described in WO 2005/079123 A2 as well as corona discharges, magnetron discharges or glow discharges as described in Bogaerts et al., Spectrochimica Acta Part B 57 (2002) 609-658.

In general terms, three reactive species as understood here and henceforth co-exist in plasmas that need to be considered especially with respect to a treatment effect:

a) Electric forces, originating from ions, electrons and/or excited molecules;
b) photons, in particular UV-photons or UV-radiation;
c) compounds, in particular contaminants, suchlike reactive chemical species, in particular radicals, airborne microbes and chemical toxins in general, in particular VOC, pollen, bacteria, spores or viruses.

It has now been found that the combination of the plasma-generating device and the dielectric structure provides a synergistic effect: the plasma-generating device for the generation of a plasma according to the invention has the advantage that this generated plasma is better suited to treat most compounds; although the invention is not limited thereby, it is understood that the conveyance of the plasma into a dielectric structure will sustain the plasma over a greater length and modify the plasma, thereby extending the time the plasma can react with the compounds and/or improve the treatment.

Although the invention is not limited thereby, the synergistic effect could be explained as follows: the generation of a surface wave between the plasma and the dielectric structure modifies the plasma such that at least a fraction of the electrons in the plasma is accelerated to higher velocities by the surface wave, leading to the improved treatment effect.

This arrangement of the plasma-generating device and the dielectric structure has the further advantage that the achieved treatment of the gaseous medium is energy-efficient, because the energy fed into the plasma-generating device for the plasma generation is efficiently converted into photons and electric forces originating from ions, electrons and/or excited molecules without generating considerable waste heat.

Such a device might be e.g. incorporated into ventilation and/or air conditioning systems or might be used as a stand-alone device, in particular as a reaction vessel, for the treatment of air.

Preferably, the device comprises in flow direction downstream of the at least one dielectric structure, an interaction-chamber with an interior space with at least one wall.

This interaction-chamber has the advantage that the duration of the interaction between the reactive species of the plasma is increased, i.e. a prolongation of the reaction time occurs, thus increasing the treatment effect.

A further advantage of this interaction-chamber is the amplification of the number of photons, i.e. the photon species of the plasma. Although the invention is not limited thereby, the effect is currently understood as follows: photons are in particular generated by slowing high velocity electrons, so called Bremsstrahlung, conveyed into the interaction-chamber from the dielectric structure due to the interaction between said high velocity electrons with the electric field in the interaction-chamber.

More preferably, the at least one wall of the interaction-chamber exhibits at least a partial diamond coating. Preferably, the at least one wall exhibits a complete diamond coating on the interior space side.

This has the advantageous effect that the photons, i.e. the electromagnetic radiation, are dispersed in the plasma more efficiently thus increasing the treatment effect caused by said photons. In particular, the at least partial diamond coating supports the amplification of the number of photons. Furthermore, Raman, i.e. inelastic, scattering of photons on the diamond coating in particular leads to an increase of the energy, i.e. the frequency, of at least a fraction of the scattered photons.

It is known in the art that it is possible to excite primary and secondary electron-hole pairs in diamonds with photons as e.g. explained by Gaudin et al., photoconductivity and photoemission of diamond under femtosecond VUV radiation (2005), Scientific Commons, http://en.scientificcommons.org/27223646. Although the invention is not limited thereby, it is currently understood that primary and secondary electron-hole pairs are excited in the diamond coating which then recombine by emitting two photons thus amplifying the number of photons in the interaction-chamber further.

As an alternative to a, in particular natural, diamond coating, zirconium oxide and/or other synthetic diamond coatings are usable. In particular, a diamond coating with a nitrogen dopant is usable.

It is known in the art that doping diamond with nitrogen may create so-called charged nitrogen-vacancy colour centres which may be excited by visible light, which subsequently generates luminescence as e.g. explained by Han et al., Three-Dimensional Stimulated Emission Depletion Microscopy of Nitrogen-Vacancy Centres in Diamond Using Continuous-Wave Light, Nano Letters, 2009, Vol. 9, No. 9, 3323-3329. Although the invention is not limited thereby, it is currently understood that this leads to the more efficient dispersion of the photons in the plasma.

Preferably, the interaction-chamber comprises an amplification structure, which is in particular perforated. In particular, the amplification structure is formed conically in the average flow direction of the gaseous medium. Preferably, the amplification structure is formed as an epicycloid. The amplification structure comprises at least a partial, preferably a complete diamond coating.

The term "perforated" has in the context of the present invention the meaning that the structure has openings through which air and/or plasma can pass. In the context of the present invention, the term "average flow direction" has the meaning of the average direction from the interaction-chamber inlet to the interaction-chamber outlet, i.e. substantially parallel to the longitudinal axis of the interaction chamber.

The term "epicycloid" has in the context of the present invention the meaning that along a projection in the average flow direction the amplification structure has an outer shape formed as an epicycloid. The arrangement of the amplification structure in the interaction-chamber has the advantage that the surface exhibiting a diamond coating is increased with the advantageous effect as already set out above. Furthermore, the conical shape of the amplification structure has the advantage that the flow of the gaseous medium is directed to the interaction-chamber outlet, which increases the plasma density, i.e. the number charged particles in the plasma, downstream of the interaction-chamber for further use More preferably, a substantially cylindrical structure is arranged in the volume enclosed by the conically formed amplification structure, wherein the cylindrical structure comprises at least a partial, preferably a complete diamond coating. The cylindrical structure is in particular perforated. In particular, the longitudinal axis of the cylindrical structure is substantially parallel to the average flow direction and preferably runs along the longitudinal axis of the interaction-chamber.

This has the advantage of further increasing the surface exhibiting a diamond coating with the advantages as set out above and to direct the gaseous medium more effectively towards the interaction-chamber outlet.

Preferably, no microwave radiation is supplied to the at least one dielectric structure.

More preferably, the interaction-chamber comprises at least one electrode. In particular, a voltage is applied to the at least one electrode.

The advantage of the presence of the at least one electrode is to increase the degree of ionisation of the plasma and thus to increase the treatment effect.

In particular, a voltage in the range of 5 kV to 12 kV is applied to the at least one electrode. This has the further advantage of supporting the plasma generation and/or maintaining the plasma present in the interaction-chamber.

Preferably, a voltage can be applied to the amplification structure in such a way that the amplification structure functions as a counter-electrode to the electrode comprised in the interaction-chamber, in particular in such a way that the electrode functions as a cathode and the amplification structure functions as an anode.

Although the invention is not limited thereby, this is currently understood to have the advantageous effect according to the theory of magneto-hydrodynamics that, due to the electromagnetic forces and the form of the amplification structure in the interaction-chamber, the generation of further turbulence and thus an improved homogeneity of the plasma for improved treatment efficiency can be achieved; this is further understood to generate electromagnetic forces in the interaction-chamber for conveying the plasma more efficiently into the further dielectric structures downstream of the interaction-chamber; it is further understood that similar effects occur in the plasma-generating device for generating an improved homogeneity of the plasma for improved treatment efficiency and for generating electromagnetic forces in the plasma-generating device for also conveying the plasma more efficiently into the dielectric structures downstream of the plasma-generating device; this results in an efficient conveyance of the air and/or plasma through the device according to the invention.

Most preferably, the at least one electrode exhibits a partial diamond coating, preferably a complete diamond coating.

This diamond coating has the same advantageous effect as already set out above.

As an alternative to a, in particular natural, diamond coating, zirconium oxide and/or other synthetic diamond coatings are usable. In particular, a diamond coating with a nitrogen dopant is usable.

It is especially preferred that the device comprises in flow direction of the gaseous medium downstream of the interaction-chamber at least one further dielectric structure. In particular, the device comprises at least one further fused silica tube. The plasma is conveyable into the at least one further dielectric structure from the interaction-chamber.

This at least one further dielectric structure has the similar advantageous effect as already set out above.

Preferably, the device comprises in flow direction of the gaseous medium downstream of the at least one further dielectric structure a further chamber for the extinction of the plasma.

This further chamber, i.e. a relaxation chamber, has the advantageous effect that the reactive species of the plasma are able to recombine in this chamber thus extinguishing the plasma. Hence, only a substantially neutral gaseous medium exits the further chamber substantially without radicals thus posing no danger for the environment.

Most preferably, the further chamber exhibits in flow direction a tapered section inside the chamber.

This has the advantageous effect that the likelihood of interaction between the species of a plasma is increased thus increasing the likelihood of recombination to achieve a substantially neutral gaseous medium.

It is especially preferred that at least one of the dielectric structures is coated inside at least partially, preferably completely, with a pigment for wavelength conversion of electromagnetic radiation to longer wavelength.

This has the advantage that it is possible to adjust the wavelength of the photons in the plasma in respect of the contaminants in the gaseous medium to be sterilized, in particular airborne microbes or chemical toxins. This is for instance advantageous in environments with known contaminants as for instance buildings with air conditioning equipment. It is thus possible to implement the device according to the present invention in e.g. an air conditioning system and to adapt it to the expected contaminants.

Preferably, the device comprises means for conveying a reaction gas into the device.

This has the advantage that the plasma generation can be improved, i.e. by increasing the degree of ionization of the plasma or reducing the amount of energy necessary when keeping the degree of ionization substantially constant. For example, helium is usable as a reaction gas. In particular, this allows for the synthesis of new products like $H_2$ by reduction of VOC.

More preferably, the interaction-chamber comprises means for the amplification of photons. In particular, photons of a selected wavelength are amplified.

This has the beneficial effect that the amount of photons, i.e. the amount of one of the reactive species of the plasma, is increased in the plasma, i.e. the photons are amplified. This amplification leads to an improved treatment effect. It is particularly beneficial to amplify the number of photons of a selected wavelength or wavelength-range which are especially suited for treatment of certain known contaminants, e.g. matching the wavelength, i.e. energy, of the photons to be amplified with the necessary energy to decompose or break up certain contaminants known to be comprised in the plasma.

In particular, the plasma-generating device comprises crystals for the amplification of the number of photons in the plasma-generating device. Examples for such crystals are fused silica crystals, which are in particular optically pumped by e.g. a ruby laser.

Preferably, the device comprises means for uncoupling photons, in particular UV photons.

The means for uncoupling photons comprise windows, in particular UV-transparent windows. For example, the at least one dielectric structure, in particular the at least one further dielectric structure, may be formed as a window for uncoupling photons.

This has the advantageous effect that photons can be uncoupled from the device, in particular for the treatment of a liquid, solid, surface or any combination thereof. In particular, water can be treated. With other words, the device can be used a photon source.

More preferably, the device comprises at least one plasma-device inlet for conveying the gaseous medium into the plasma-generating device, wherein the plasma-device inlet exhibits in flow direction a tapered inlet-section.

This has the advantage that the velocity of the gaseous medium conveyed into the plasma-device inlet is increased thus increasing the turbulence in the plasma-generating device. Furthermore, this makes it possible to convey the gaseous medium at lower velocities into the plasma-generating device and still achieve the required turbulence for generating a substantially even plasma density in the plasma-generating device by increasing the velocity of the gaseous medium. The turbulence improves the distribution of the plasma in the plasma-generating device thus achieving a substantially even plasma density.

Most preferably, the device comprises at least one plasma-device inlet for conveying the gaseous medium into the plasma-generating device, wherein a deflector for the gaseous medium for generating turbulence in the flow of the gaseous medium is arranged downstream of the plasma-device inlet.

It is thus possible to have a device with a tapered inlet-section in the plasma-device inlet and no deflector, a tapered inlet-section in the plasma-device inlet and a deflector and no tapered inlet-section in the plasma-device inlet and a deflector.

The use of a deflector for the gaseous medium has the advantage of generating increased turbulence in the flow of the gaseous medium which improves the generation of a substantially even plasma density in the plasma-generating device, i.e. a more homogeneous plasma.

The deflector can be formed as any geometric feature in the plasma-generating device for deflecting and/or channelling the flow of the gaseous medium, i.e. a curved wall segment.

Preferably, the plasma-device inlet and/or the deflector comprise at least one guiding channel for the gaseous medium, in particular a helically formed guiding channel.

This has the advantage that the gaseous medium is at least partly guided by the guiding channel generating a vortex in the flow which increases the turbulence in the plasma-generating device for a more homogeneous plasma. A further advantage is an increased residence time of at least a part of the gaseous medium in the plasma-generating device due to the longer flow path in the guiding channels of the gaseous medium. This results in a more efficient plasma generation and an improved treatment efficiency in the plasma-generating device.

The guiding channel is in particular formed as a groove in the wall of the plasma-device inlet and/or the deflector.

Preferably, the device comprises a magnetron with at least a first magnetron-electrode and at least one counter-electrode, wherein at least one further electrode is arranged in the plasma-generating device in a zone formed by a projection of the plasma-device inlet along the average flow of the gaseous medium through the plasma-device inlet, wherein in particular turbulent flow is generable in the zone by the deflector.

With other words, the further electrode is arranged where the gaseous medium enters the plasma-generating device for generating a plasma in the gaseous medium just conveyed into the plasma-generating device. This further enhances the plasma-generating capabilities of the plasma-generating device.

More preferably, the deflector is arranged such that the deflector does not prevent line of sight between the counter-electrode and the further electrode, in particular along the shortest straight line connecting the counter electrode and the further electrode.

This has the advantage that the deflector does not impair the plasma generation.

The phrase "shortest straight-line" connecting the counter electrode and the further electrode means a virtual line drawn between the counter electrode and the further electrode.

Most preferably, the plasma-generating device comprises at least one wall with a fused silica surface inside the plasma-generating device, in particular the wall opposite the plasma-device inlet.

The arrangement of a fused-silica surface inside the plasma-generating device has the same advantage as explained for the dielectric structures downstream of the plasma-generating device in respect of the possible acceleration of a fraction of the electrons to higher velocities by a surface wave, although the invention is not limited thereby.

It is preferred that the inner space of the plasma-generating device is in at least one section substantially convergent in flow direction and the interior space of the interaction-chamber is in at least one section substantially divergent in flow direction for increasing the turbulence in the device and in particular the homogeneity of the plasma.

With other words, the dimension substantially perpendicular to the average flow is decreasing in at least in one section in the plasma-generating device and increasing in at least in one section in the interaction-chamber.

This has the advantage of further increasing treatment efficiency of the gaseous medium in the device.

Another aspect of the present invention is a method for treatment of a gaseous medium, in particular air. This method is carried out in particular with a device as described above. This method comprises the steps of generating a plasma in a plasma-generating device in the gaseous medium and conveying the plasma into at least one dielectric structure.

This method is preferably implemented with a device according to the present invention. Hence, the method for treatment of a gaseous medium according to the invention has the same advantages as set out above.

Preferably, the method comprises the step of conveying the plasma into an interaction-chamber downstream of said at least one dielectric structure. Optionally, the plasma is conveyed into at least one further dielectric structure downstream of the interaction-chamber. Preferably, the plasma is conveyed into a further chamber downstream of the at least one further dielectric structure.

According to another aspect of the invention, the device as described above is operated with the above method according to the invention for the treatment of a gaseous medium, in particular air and/or methane. In particular, $CO_2$, in particular mixed with steam and/or other gases, preferably combustion gases, can be reformed.

It is known in the art to use plasma technologies for reducing $CO_2$ emissions as described by Morvová et al, (Journal of thermal analysis and calorimetry, volume 61 (2000) 273-287) and by Morvová et al. (Utilisation of $CO_2$, fixation of nitrogen and exhaust gas cleaning in electric discharge with electrode catalysis). It is furthermore known in the art to synthesise amino-acid precursors from simulated planetary atmospheres by vacuum ultraviolet light (Takahashi at al., Journal of applied physics, July 2005, volume 98, issue 2) as well by Civiš et al. (Chemical Physics Letters 386 (2004) 169-173).

A further aspect of the invention is the operation of a device as described above with the above method for the treatment of liquids, solids, surfaces or any combination thereof, in particular with UV photons uncoupled from the device. Alternatively, the treatment of liquids, solids, surfaces or any combination thereof is achievable with the gaseous medium treated in the device according to the invention which exits said device.

Another aspect of the present invention is the operation of a device as set out above with the above method for reforming methanol, in particular for producing hydrogen.

The use of the device has the advantageous features as set out above for the device and the method.

It is known in the art to reform ethanol and methane in a microwave surface-wave plasma discharge as described by Yanguas-Gil et al. (applied Physics Letters, volume 85, no. 18, 1. Nov. 2004) and by Jasinski et al. (Chem. Listy 102, S. 1332-S. 1337 (2008); II Central European Symposium on Plasma Chemistry 2008).

A further aspect of the present invention is directed to a magnetron for use in a device as described above comprising a first magnetron-electrode, a counter-electrode and a loop-shaped electrode in the form of a closed loop, in particular ring-shaped, enveloping an area, and wherein the first magnetron-electrode is arranged in the area, in particular substantially in the centre, a further electrode is arranged outside the area. The loop-shaped electrode comprises at least one inward-member arranged in the area, wherein the inward-member is arranged substantially parallel to an axis perpendicular to the loop-shaped electrode between the loop-shaped electrode and the first magnetron-electrode and at least one outward-member arranged outside the area substantially parallel to an axis perpendicular to the loop-shaped electrode between the loop-shaped electrode and the further electrode.

This has the advantage, in particular when used in the device described above, that the plasma-generation is improved.

With other words in case of a ring-shaped electrode, the axis perpendicular to the ring-shaped electrode is the radius. The axis between the ring-shaped electrode and the further electrode is meant to be the axis that starts where the outward-member is arranged or formed on the ring-shaped electrode. In particular for a ring-shaped electrode, the outward-member and the inward-member are arranged substantially parallel to the radius of the ring-shaped electrode.

This arrangement of at least one inward-member and at least outward-member on the loop-shaped electrode has the advantage of further increasing the efficiency of the plasma-generation.

Most preferably, the loop-shaped electrode comprises at least two inward-members, wherein one of the inward-members exhibits a first length and the other of the inward-members exhibits a second different length. In particular, the ratio of the inward-members of different length is 1.5:1 and preferably 2:1.

This has the advantage of further supporting the plasma-generation.

Preferably, the at least one inward-member and the at least one outward-member are arranged on the loop-shaped electrode at different positions along the loop. In particular, the magnetron comprises at least two outward-members and at least two inward-members, wherein a distance along the loop between the inward-member and the outward-member is substantially ¼ of the circumference of the loop. More preferably, the magnetron comprises at least n outward-members and at least n inward-members, wherein a distance along the loop between the inward-member and the adjacent outward-member is substantially 1/(2*n) of the circumference of the loop. For instance, if the magnetron comprises n=8 inward and outward members, the distance along the loop is 1/16.

This has the advantage of a further improved plasma generation and the generation of an even more substantially even plasma density in the plasma-generating device.

In particular, water, preferably potable water, can be treated with the device.

These uses of the device have the same advantageous features as set out above for the device and the method.

Yet another aspect of the present invention is a device for the treatment of a gaseous medium, in particular with the device as described above, comprising an inlet and an outlet for the gaseous medium. The device furthermore comprises means for amplification of photons. In particular, photons of a selected wavelength or wavelength-range are amplified. In addition, the device comprises means for the generation of plasma.

This device has the beneficial effects as set out above.

Further objects, advantages and novel features according to the invention will become apparent from the following detailed description of the preferred embodiments, accompanied by the following schematical drawings.

Figure 1:
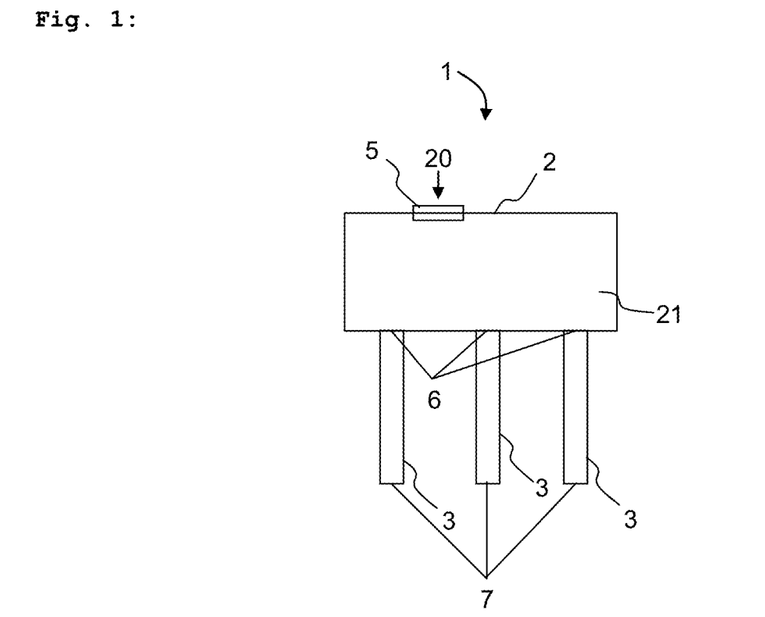
FIG. 1: Schematic overview of a device for the treatment of air according to the invention comprising a plasma-generating device and dielectric tubes.

FIG. 1 shows a device 1 for the treatment of air comprising a plasma-generating device 2 for the generation of a plasma 21. The plasma-generating device 2 is a device as suggested in WO 2005/079123 A2.

Air 20 is conveyed into the plasma-generating device 2 by external means not shown in the schematic drawing. However, conveying means may include inter alia external ventilation means.

Air 20 is conveyed into the plasma-generating device 2 through plasma-device inlet 5. Inside the plasma-generating device 2 a plasma 21 is generated in the air 20, i.e. air 20 is converted into plasma 21. The plasma 21 exhibits atmospheric pressure, i.e. pressure in the range of 0.8 bar to 1.2 bar, and a temperature in the range of 15° C. to 45° C.

The plasma 21 is conveyed through plasma-device outlets 6 into three fused silica tubes and is subsequently conveyed along the fused silica tubes to the interaction-chamber inlet 7. This has the effect of accelerating at least a fraction of the electrons in the plasma 21. This plasma 21 as modified in the fused silica tubes 3 interacts with contaminants suchlike airborne microbes or chemical toxins thus reducing the amount of such contaminants in the plasma 21. Hence, the plasma 21 exiting interaction-chamber inlet 7 contains a lower degree of contaminants.

Figure 2:
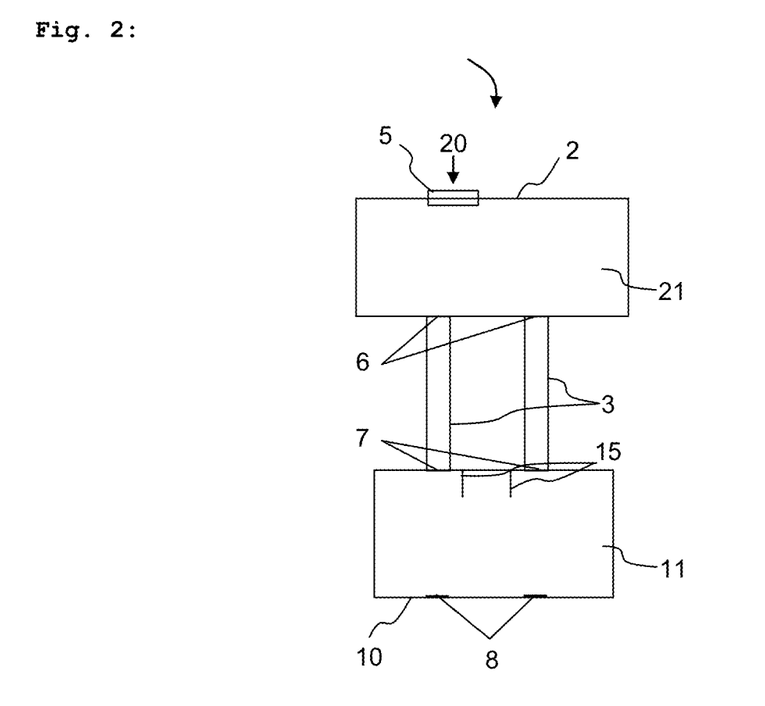
FIG. 2: Schematic overview of an alternative embodiment of the device for the treatment of air according to the invention comprising a further interaction-chamber.

FIG. 2 shows an alternative schematic overview of the device 1 for the treatment of air with a further interaction-chamber 10. The alternative embodiment of the invention according to FIG. 2 comprises elements already described in FIG. 1 which will not be explained further here. From here an henceforth, parts with the same reference numeral denominate the same parts in the figures.

Plasma 21 exits the two fused silica tubes 3 through interaction-chamber inlet 7 and is conveyed into the interaction-chamber 10 with an interior space 11. In the interaction-chamber 10, two electrodes 15 are placed inside the interior space 11. The electrodes 15 are coated with a complete diamond coating. A voltage of 10 kV is applied to the electrodes 15 with a power supply (not shown). This has the effect of supporting the plasma generation and maintaining the plasma present in the interaction-chamber.

In the interior space 11 of the interaction-chamber 10, the plasma 21 interacts further with the contaminants comprised in the plasma 21 thus reducing the amount of contaminants in the plasma 21 even further.

Plasma 21 is subsequently conveyed through two interaction-chamber outlets 8.

Figure 3:
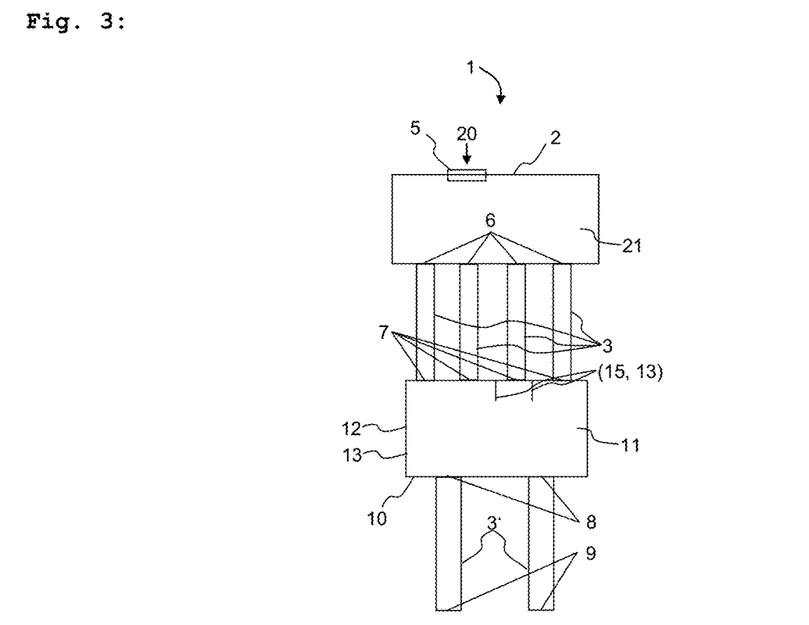
FIG. 3: Schematic overview of a further alternative device for the treatment of air according to the invention comprising further dielectric tubes.

FIG. 3 shows a schematic overview of a further device 1 for the treatment of air. FIG. 3 shows a similar device 1 as depicted in FIG. 1 and FIG. 2 with further fused silica tubes 3' downstream of an interaction-chamber 10. Same reference numerals denominate the same parts as in FIG. 1 and FIG. 2.

The plasma 21 exits the interaction-chamber 10 through interaction-chamber outlets 8 and is conveyed into further fused silica tubes 3'. These fused silica tubes 3' have the same function as the fused silica tubes 3 upstream of the interaction-chamber 10. The plasma 21 subsequently exits the further fused silica tubes 3' through further-chamber inlets 9.

Interaction-chamber 10 has a wall 12 with a diamond coating 13. The electrodes 15 are coated with a complete diamond coating 13.

Figure 4:
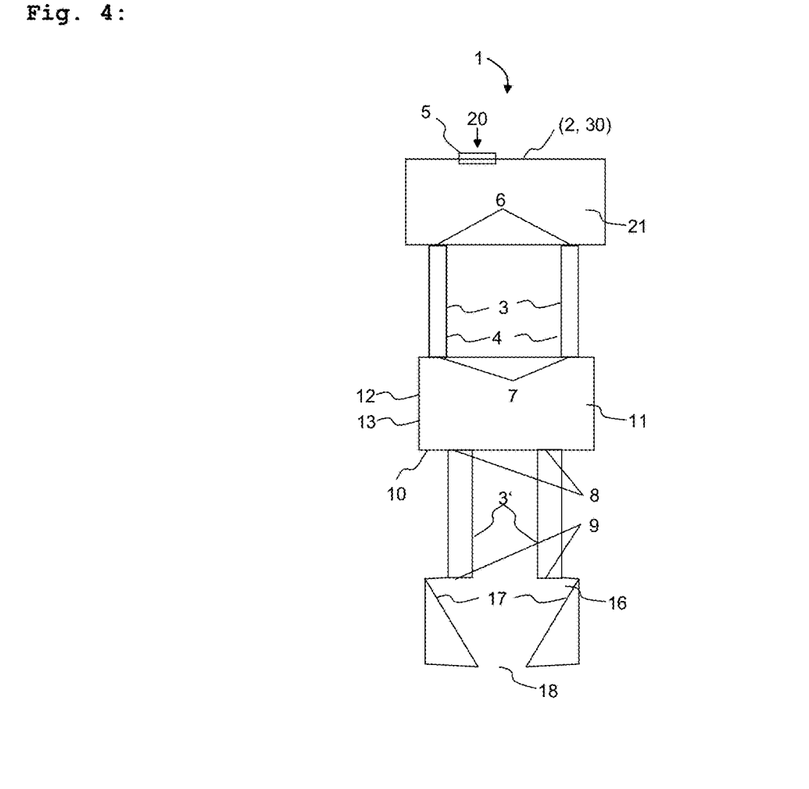
FIG. 4: Schematic overview of another alternative device for the treatment of air according to the invention comprising an additional, i.e. relaxation chamber.

FIG. 4 shows a further schematic overview of a device 1 for the treatment of air according to the invention comprising a further chamber 16, i.e. a relaxation chamber, for the extinction of the plasma 21.

The device 1 for the treatment of air comprises a plasma-generating device. This plasma-generating device 2 is a magnetron 30. Air 20 is conveyed by external ventilation (not shown) into the plasma-generating device 2 through plasma-device-inlet 5. In the plasma-generating device 2 a plasma 21 is generated with the magnetron. This plasma 21 exhibits a pressure in the range of 0.7 to 1.3 bar and a temperature in the range of 20° C. to 40° C. Plasma 21 is conveyed through plasma-device-outlets 6 into the fused silica tubes 3 which exhibit a coating with pigments 4 for wavelength conversion of electromagnetic radiation to longer wavelength.

Subsequently, plasma 21 is conveyed into interaction-chamber 10 through interaction-chamber-inlet 7. The interaction-chamber 10 has an interior space 11 and a wall 12 coated with a complete diamond coating 13. The whole interior space 11 is coated. The plasma 21 interacts with the contaminants comprised in the flow, wherein the plasma 21 is subsequently conveyed into fused silica tubes 3'.

Plasma 21 is subsequently conveyed through further-chamber inlets 9 into a further chamber 16 for the extinction of the plasma 21.

The further chamber 16 exhibits in flow direction a tapered section 17. The flow of air 20, which is substantially not plasma 21 anymore in the vicinity of further-chamber outlet 18, exits the device 1 through said further-chamber outlet 18.

Figure 5:
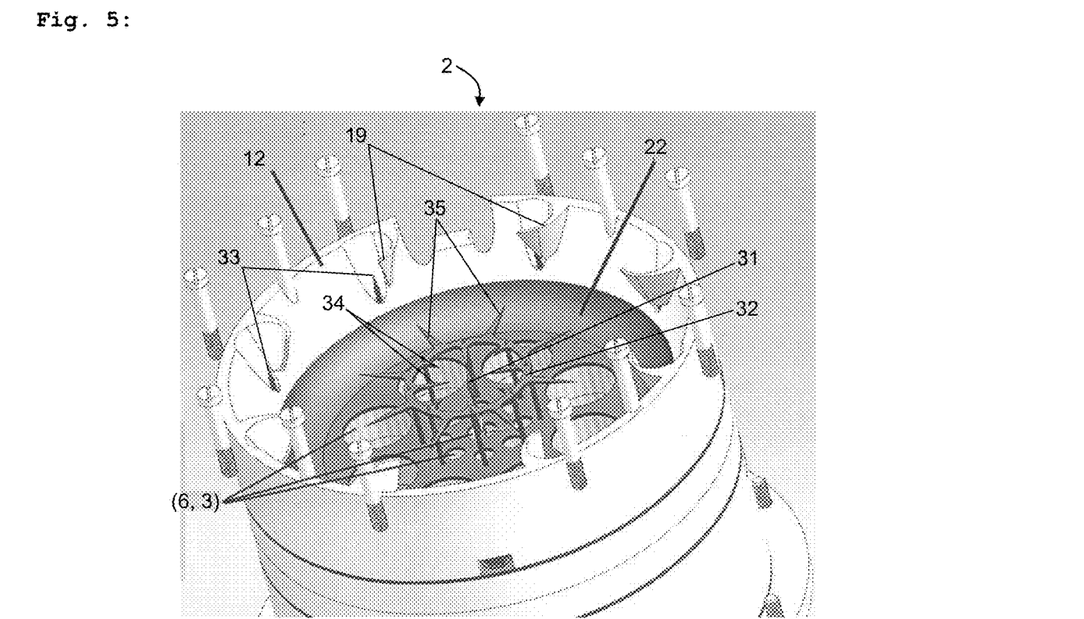
FIG. 5: perspective overview of an alternative embodiment of an alternative embodiment of the plasma-generating device.

FIG. 5 shows a plasma-generating device with a wall 12 with several deflectors 19 for generating turbulence in the flow of the air conveyed into the plasma-generating device 2. The plasma-generating device 2 further comprises a fused-silica surface 22 arranged opposite of the plasma-device inlet (not shown). Further electrodes 33 are arranged in the plasma-generating device in a zone formed by a projection of the plasma-inlet (not shown) along the average flow direction of the gaseous medium through the plasma-device inlet.

In the wall exhibiting the fused-silica surface, plasma-device outlets 6 and dielectric structures 3 are arranged for conveying the plasma out of the plasma-generating device.

The plasma-generating device 2 comprises furthermore a magnetron-electrode 31 and a loop-shaped electrode 32 with outward-members 35 and inward-members 34. The loop-shaped electrode 32 is ring-shaped. The outward-members 35 are arranged such that they are each arranged parallel to a straight line connecting the magnetron-electrode 31 and a further electrode 33.

The inward-members 34 are each arranged parallel to a straight line connecting the magnetron-electrode 31 and the loop-shaped electrode 32. The inward-members 34 exhibit different lengths, wherein one type of inward-member is twice as long as the shorter inward-member type, i.e. the ratio is 2:1.

Figure 6:
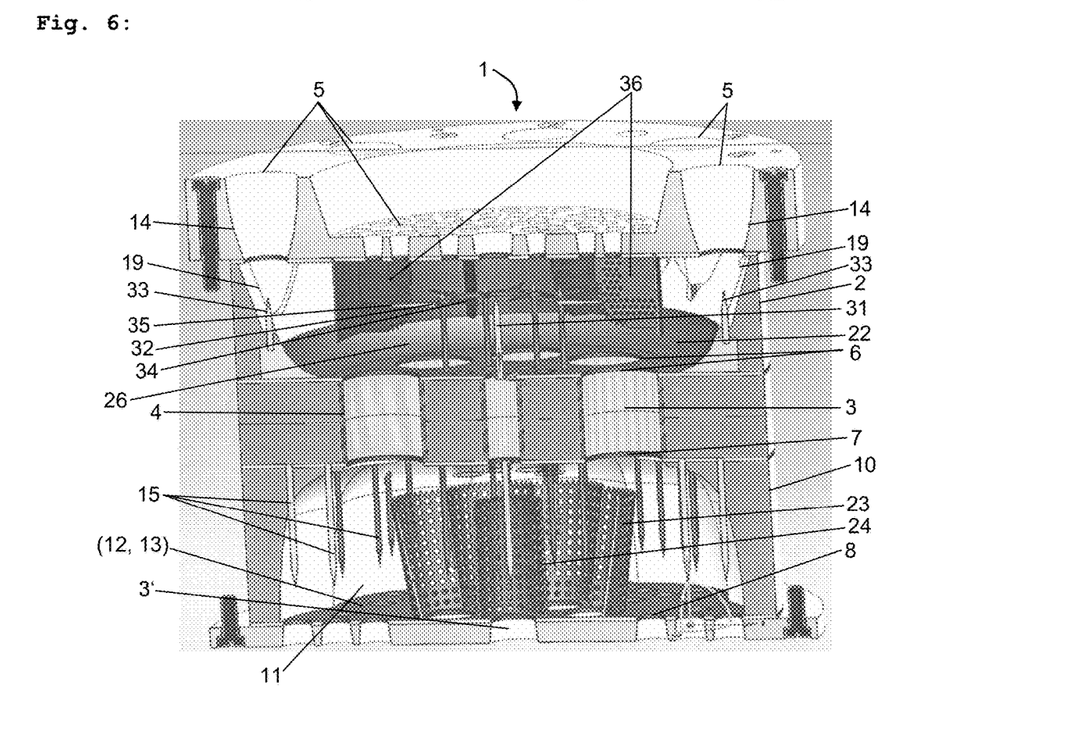
FIG. 6: plan view of a device for the treatment of air according to the invention comprising a plasma-generating device, dielectric tubes and a further interaction-chamber.

FIG. 6 shows an alternative embodiment of the device 1 for the treatment of a gaseous medium according to the present invention with a plasma-generating device 2 and a further chamber 10.

The plan view as shown in FIG. 6 comprises the plasma-generating device as depicted in FIG. 5. Downstream of the plasma-generating device, fused-silica tubes 3 which exhibit a coating with pigments 4 for wavelengths conversion of electromagnetic radiation to a longer wavelength.

The plasma-device inlet 5 exhibits in flow direction a tapered inlet-section 14.

Counter-electrode 36 in the form of a ring with wall sections arranged substantially parallel to the radius of the ring with a perforated wall is also shown.

The plasma can be conveyed through the interaction-chamber inlet 7 into the interaction-chamber 10 where electrodes 15 are arranged for maintaining the plasma in the interaction-chamber 10.

The interaction-chamber 10 furthermore comprises an amplification structure 23 in the form of an epicycloid and a cylindrical structure 24 arranged in the volume enclosed by the amplification structure 23 the amplification structure, the cylindrical structure and the wall 12 each exhibit a diamond coating 13.

The plasma is conveyed through interaction-chamber outlets 8 into fused-silica tubes 3'.

The inner space 26 is substantially convergent in the average flow direction of the gaseous medium and the interior space 11 of the interaction-chamber 10 is substantially divergent in the average flow direction of the gaseous medium.

Figure 7:
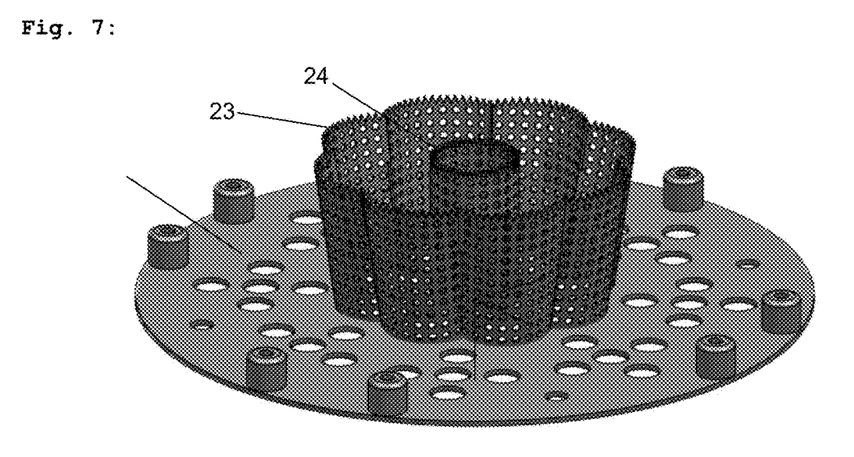
FIG. 7: perspective view of an amplification structure for use in the interaction-chamber.

FIG. 7 depicts a perspective view of the amplification structure 23, cylindrical structure 24 and a wall 12, wherein the amplification structure 23, the cylindrical structure 24 and the wall 12 each exhibit a diamond coating.

Figure 8:
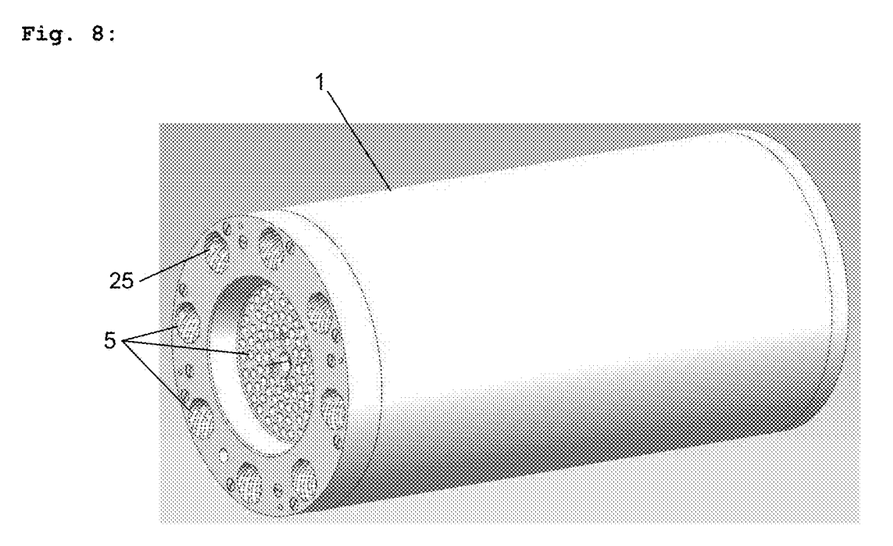
FIG. 8: perspective view of the encapsulated device.

FIG. 8 depicts an encapsulated device 1. Here, only the plasma-device inlets 5 are visible. The plasma-device inlets 5 arranged adjacent to the outer radius have guiding channels 25 formed helically in the walls.

Figure 9:
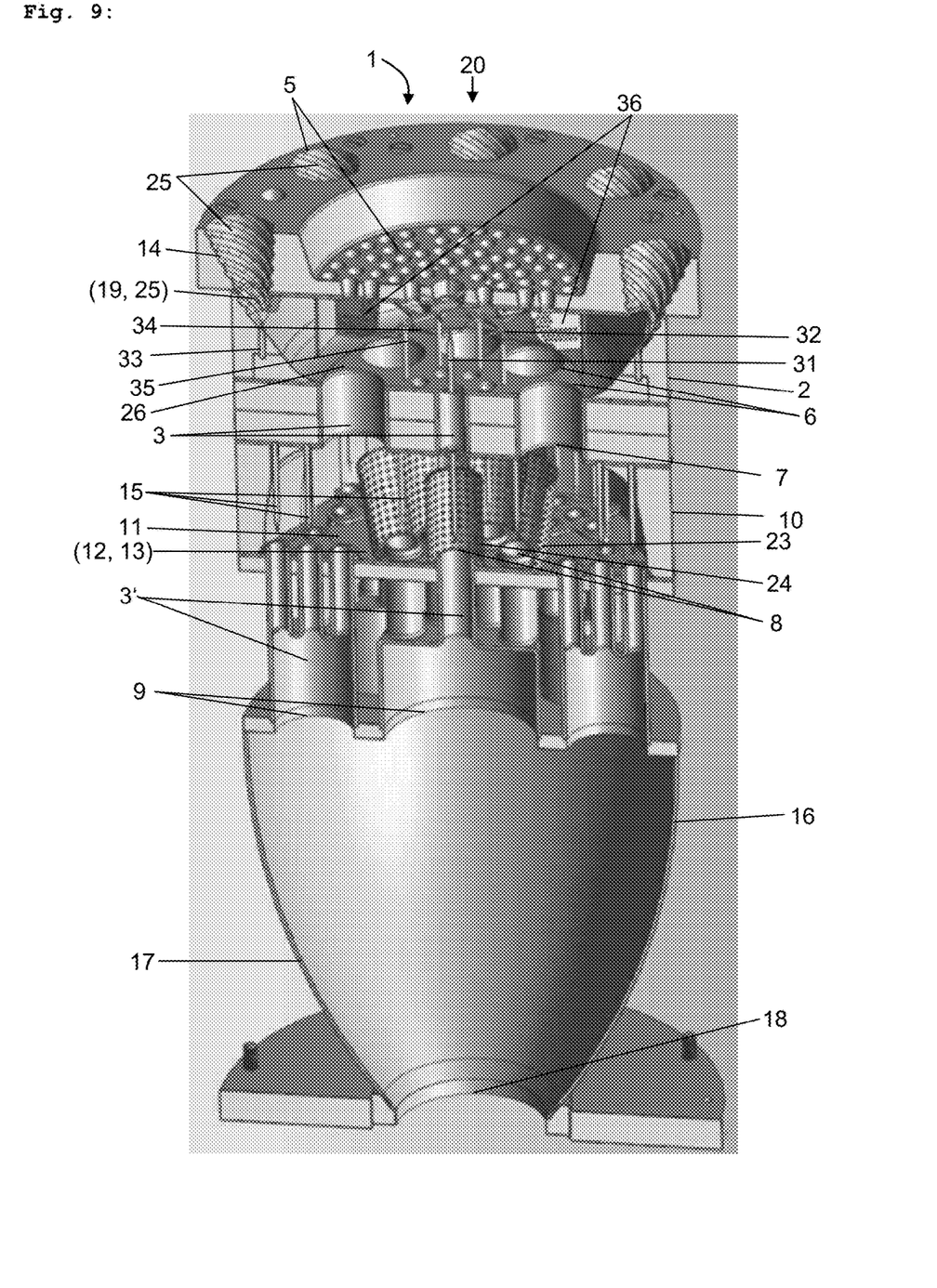
FIG. 9: plan view of the encapsulated device according to FIG. 8.

FIG. 9 depicts a plan view of the device 1 according to FIG. 8. The device 1 according to FIG. 9 has a similar configuration as the device shown in FIG. 6 between the plasma-device inlets 5 for conveying air 20 into the device 1 and the interaction-chamber outlets 8.

The device 1 according to FIG. 9 has in addition to the device shown in FIG. 6 guiding channels 25 in the plasma-device inlets 5 and the deflector 19 for increasing the turbulence in the flow.

Downstream of the interaction-chamber outlets 8 are arranged further dielectric structures 3' in the form of dielectric tubes which are in flow communication with the further-chamber inlets 9.

The plasma can be conveyed through further-chamber inlets 9 into further chamber 16. The further chamber 16 exhibits a tapered section 17 for conveying the treated gaseous medium, which is substantially not plasma anymore, through further-chamber outlet 18 out of the device 1.

The invention claimed is:

1. A device for the treatment of a gaseous medium, wherein the device comprises in a flow direction of the gaseous medium:
   a plasma-generating device for generation of a plasma in the gaseous medium,
   at least one dielectric structure formed as least one fused silica tube,
   wherein the plasma is conveyable into the at least one dielectric structure,
   an interaction-chamber with an inferior space with at least one wall is located downstream of the at least one dielectric structure, and
   the at least one wall exhibits at least a partial diamond coating on an inwardly facing surface thereof.

2. The device according to claim 1, wherein no microwave radiation is applied to the at least one dielectric structure.

3. The device according to claim 1, wherein the interaction-chamber comprises at least one electrode.

4. The device according to claim 3, wherein the at least one electrode exhibits a partial diamond coating.

5. The device according to claim 1, wherein the interaction-chamber comprises an amplification structure, and the amplification structure comprises at least a partial diamond coating.

6. The device according to claim 5, wherein a substantially cylindrical structure is arranged in a volume enclosed by the amplification structure, which is conically formed, and the cylindrical structure comprises at least a partial diamond coating.

7. The device according to claim 1, wherein the device comprises, in a flow direction of the gaseous medium downstream of the interaction-chamber, at least one further dielectric structure, and the plasma is conveyable into the at least one further dielectric structure from the interaction-chamber.

8. The device according to claim 7, wherein the device comprises, in the flow direction of the gaseous medium downstream of the at least one further dielectric structure, a further chamber for extinction of the plasma.

9. The device according to claim 8, wherein the further chamber exhibits, in the flow direction, a tapered section inside the further chamber.

10. The device according to claim 1, wherein the device comprises means for conveying a reaction gas into the device.

11. The device according to claim 1, wherein the interaction-chamber comprises means for amplification of photons.

12. The device according to claim 1, wherein the device comprises at least one plasma-device inlet for conveying the gaseous medium into the plasma-generating device, and the at least one plasma-device inlet exhibits, in the flow direction, a tapered inlet-section.

13. The device according to claim 1, wherein the device comprises at least one plasma-device inlet for conveying the gaseous medium into the plasma-generating device, and a deflector for the gaseous medium for generating turbulence in the flow of the gaseous medium is arranged downstream of the at least one plasma-device inlet.

14. The device according to claim 13, wherein the plasma-generating device comprises a magnetron with at least a first magnetron-electrode and at least one counter-electrode, and at least one further electrode is arranged in the plasma-generating device in a zone formed by a projection of the plasma-device inlet along an average flow of the gaseous medium through the plasma-device inlet.

15. The device according the claim 14, wherein the at least one counter-electrode comprises a first counter-electrode and the at least one further electrode comprises a first further electrode, and the deflector is arranged such that the deflector does not prevent a line of sight between the first counter-electrode and the first further electrode.

16. The device according to claim 1, wherein an inner space of the plasma-generating device is in at least one section substantially convergent in an average flow direction of the gaseous medium and the interior space of the interaction-chamber is in at least one section substantially divergent in the average flow direction of the gaseous medium for increasing turbulence in the device.

17. The device according to claim 1, wherein the plasma-generating device comprises at least one wall with a fused silica surface inside the plasma-generating device.

18. A device for the treatment of a gaseous medium, wherein the device comprises in a flow direction of the gaseous medium;
   a plasma-generating device for generation of a plasma in the gaseous medium,
   at least, one dielectric structure formed as at least one fused silica tube,
   wherein the plasma is conveyable into the at least one dielectric structure,
   an interaction-chamber with an interior space with at least one wall is located downstream of the at least one dielectric structure, and
   the plasma-generating device comprises a magnetron with a first magnetron-electrode, a counter-electrode and a loop-shaped electrode in a form a closed loop enveloping an area, the first magnetron-electrode is arranged in the area, a further electrode is arranged outside the area, the loop-shaped electrode comprises at least one inward-member arranged in the area, the at least one inward-member is arranged substantially parallel to an axis perpendicular to the loop-shaped electrode, between the loop-shaped electrode and the first magnetron-electrode, and at least one outward-member arranged outside the area substantially parallel to the axis perpendicular to the loop-shaped electrode, between the loop-shaped electrode and the further electrode.

19. The device according to claim 18, wherein the loop-shaped electrode comprises at least two inward-members, and one of the at least two inward-members exhibits a first length and the other of the at least two inward-members exhibits a second different length.

20. The device according to claim 18, wherein the at least one inward-member and the at least one outward-member are arranged on the loop-shaped electrode at different positions along the loop.

* * * * *